United States Patent [19]

Matsushita et al.

[11] 4,340,090

[45] Jul. 20, 1982

[54] SILICONE COMPOSITIONS FOR THE TREATMENT OF GLASS FIBERS AND METHODS OF TREATMENT

[75] Inventors: Takao Matsushita, Kisarazu; Kazuo Hirai, Ichihara, both of Japan

[73] Assignee: Toray Silicone Company, Ltd., Tokyo, Japan

[21] Appl. No.: 295,184

[22] Filed: Aug. 21, 1981

Related U.S. Application Data

[63] Continuation-in-part of Ser. No. 146,555, May 5, 1980, abandoned.

[30] Foreign Application Priority Data

May 16, 1979 [JP] Japan .................................. 54-59088

[51] Int. Cl.³ ........................ D03D 43/00; B05D 3/02
[52] U.S. Cl. ..................................... 138/177; 65/3.41; 138/DIG. 2; 138/123; 427/387; 427/389.7; 427/389.8; 428/36; 428/266; 428/268; 428/391; 428/392; 528/15; 528/31; 528/32; 523/213; 524/837
[58] Field of Search .................. 427/387, 389.7, 389.8; 65/3.41; 138/177, DIG. 2, 123; 260/37 SB, 33.6 SB; 528/15, 31, 32; 428/35, 36, 429, 391, 392, 266, 268

[56] References Cited

U.S. PATENT DOCUMENTS

| 3,436,366 | 4/1969 | Modic ..................................... 260/37 |
| 3,491,165 | 1/1970 | Seyfried et al. ...................... 260/825 |
| 3,671,480 | 6/1972 | Wada et al. ................... 260/29.1 SB |
| 3,677,981 | 7/1972 | Wada et al. ....................... 260/2.5 S |
| 3,699,073 | 10/1972 | Wada et al. ...................... 260/37 SB |
| 3,814,723 | 6/1974 | Yokokawa et al. ............. 260/37 SB |
| 3,862,081 | 1/1975 | Itoh et al. ......................... 260/37 SB |
| 3,868,345 | 2/1975 | Kratel et al. ..................... 260/37 SB |
| 3,919,344 | 11/1975 | Merrill et al. ......................... 260/825 |
| 3,936,476 | 2/1976 | Itoh et al. ......................... 260/37 SB |
| 3,992,355 | 11/1976 | Itoh et al. ..................... 260/46.5 UA |
| 4,008,198 | 2/1977 | Krohberger et al. ........... 260/37 SB |
| 4,013,611 | 3/1977 | Hechtl et al. ................... 260/37 SB |
| 4,025,485 | 5/1977 | Kodama et al. ................ 260/37 SB |
| 4,072,796 | 2/1978 | Reinhardt et al. ................... 428/405 |
| 4,077,943 | 3/1978 | Sato et al. ..................... 260/46.5 UA |
| 4,108,825 | 8/1978 | Hayes ................................ 260/37 SB |
| 4,110,300 | 8/1978 | Matsushita ...................... 260/37 SB |
| 4,154,714 | 5/1979 | Hockemeyer et al. ........ 260/31.2 R |
| 4,177,341 | 12/1979 | Kreis et al. ............................ 528/15 |
| 4,191,587 | 3/1980 | Kratel et al. ..................... 106/308 Q |
| 4,222,983 | 9/1980 | August et al. ........................ 264/220 |
| 4,311,739 | 1/1982 | Hardman et al. ................... 427/387 |

FOREIGN PATENT DOCUMENTS

| 900660 | 5/1972 | Canada . |
| 52-63495 | 5/1977 | Japan . |
| 52-63961 | 5/1977 | Japan . |
| 1286794 | 8/1972 | United Kingdom . |
| 2001303 | 1/1979 | United Kingdom . |

Primary Examiner—John D. Smith
Assistant Examiner—Thurman K. Page
Attorney, Agent, or Firm—Roger H. Borrousch

[57] ABSTRACT

A product obtained by mixing a vinyl-containing polydiorganosiloxane, an organohydrogenpolysiloxane, a silica filler treated with dimethyldichlorosilane, optionally diphenylsilanediol, and a platinum catalyst is useful for treating glass fiber and is an electrical insulating material. The cured product has excellent electrical characteristics, flame retardancy, mechanical strength, and transparency.

21 Claims, No Drawings

SILICONE COMPOSITIONS FOR THE TREATMENT OF GLASS FIBERS AND METHODS OF TREATMENT

This is a continuation-in-part application of Ser. No. 146,555, filed May 5, 1980, now abandoned.

BACKGROUND OF THE INVENTION

1. Field of the Invention

This invention relates to a silicone composition for the treatment of glass fibers, which produces electrical insulating materials with excellent flame retardancy, electrical characteristics, mechanical strength and transparency when woven glass fiber fabrics and glass sleeves are coated or impregnated with the compositions.

2. Description of the Prior Art

Certain silicone rubber dispersion varnish compositions with excellent flame retardancy and pliability were recently proposed for treating glass fiber products useful as electrical insulating materials. For example, a silicone rubber composition described in Kokai Japanese Patent Number: Sho 52(1977)-63961, was prepared from a vinyl containing organopolysiloxane, and an organohydrogenpolysiloxane, a metal salt of an organic acid, a platinum catalyst, and fume silica filler using diphenylsilanediol as an agent for hydrophobic treatment of the silica filler. The prepared silicone rubber composition was dissolved or dispersed in an organic solvent to obtain a varnish solution in an attempt to improve flame retardancy of the varnish film. A silicone rubber composition described in Kokai Japanese Patent No. Sho 52(1977)-63495, was prepared from a vinyl containing diorganopolysiloxane, an organohydrogenpolysiloxane, fumed silica filler, hexaorganodisilazane, a platinum catalyst and optionally a silicone resin. The hexaorganodisilazane is used as an agent for hydrophobic treatment of a silica filler. The silicone rubber composition thus prepared was dissolved or dispersed in an organic solvent to obtain a varnish solution in an attempt to improve transparency of the varnish film. This varnish is useful for treating glass fiber and such treated products are said to have excellent electrical insulation properties and flame retardancy.

However, these prior art compositions are unsatisfactory in terms of transparency, workability, and bath life of the varnish solution. In the case using diphenylsilanediol as an agent for hydrophobic treatment of a silica filler, there are the drawbacks that transparency of the film and the flow characteristics of the varnish solution are impaired significantly due to the differences in compatibility and refractive index between the silicone polymer and diphenylsilanediol. In the case using hexamethyldisilazane as a surface treating agent for a silica filler, the bath life of the varnish solution is significantly reduced due to the presence of trace amounts of ammonia from the decomposition residue of hexamethyldisilazane in spite of the fact that transparency of the film can be improved due to close compatibility and similarity of refractive index between the silicone polymer and the surface of the trimethylsilylated silica. That is, a structure is formed during the storage period resulting in the drawback that the bath gels completely and loses its flowability.

SUMMARY OF THE INVENTION

To overcome the existing drawbacks of the above-mentioned compositions, this invention provides silicone compositions for the treatment of glass fibers, which have excellent electrical characteristics, mechanical strength, flame retardancy, and especially excellent workability with a low viscosity. The silicone compositions containing a silica filler which has been treated with dimethyldichlorosilane for hydrophobicity provides these stated characteristics. Diphenylsilanediol can also be included in the silicone composition to provide additional advantages. The silicone composition can be dispersed in an organic solvent, coated on glass fiber and then cured by heating to provide electrical insulation.

DESCRIPTION OF THE INVENTION

This invention relates to a silicone composition consisting essentially of a product obtained by mixing (A) 100 parts by weight of a triorganosiloxy endblocked polydiorganosiloxane in which each organic group is selected from methyl, vinyl, and phenyl, there being at least two vinyl groups per molecule, there being no more than 20 mol percent phenyl groups based on the total number of moles of organic groups in the polydiorganosiloxane and said polydiorganosiloxane having a viscosity of at least 0.1 m²/s measured at 25° C.

(B) an amount of organohydrogenpolysiloxane sufficient to provide at least 1.5 silicon-bonded hydrogen atoms per vinyl group in (a), said organohydrogenpolysiloxane having at least two silicon-bonded hydrogen atoms per molecule, and the organohydrogenpolysiloxane having organic groups selected from methyl and phenyl, (C) from 10 to 100 parts by weight of a silica filler having a relative surface area of at least 50 m²/g and having been treated with dimethyldichlorosilane for hydrophobicity, and (D) a catalytic amount of a platinum catalyst.

The triorganosiloxy endblocked polydiorganosiloxane, component (A), must be a polydiorganosiloxane having at least two vinyl groups per molecule. The vinyl groups are directly bound to silicon atoms. For example, these polydiorganosiloxanes can be expressed by the following general formula:

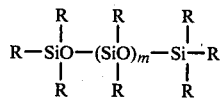

wherein each R represents an organic group selected from methyl, phenyl, and vinyl, at least two R groups per molecule are vinyl, and m is an integer. The polydiorganosiloxane, component (A), has a viscosity of at least 0.1 square meters per second (m²/s) measured at 25° C. If the polyorganosiloxane, component (A), contains phenyl groups, the proportion of phenyl groups is preferably 20 mol % or less where 100 mol % is the total number of mols of organic groups in component (A). If the proportion of phenyl groups exceeds this amount, the compatibility with the hydrophobic silica filler, component (C), becomes poor, resulting in poor transparency and flow characteristics.

The organohydrogenpolysiloxane, component (B), reacts with the above-mentioned component (A) cross-linking the polymers. In addition, flame retardancy is imparted to the woven glass fiber fabrics and glass sleeves prepared by using the compositions of this invention. The organohydrogenpolysiloxane must have at least two silicon-bonded atoms per molecule. Examples of these organohydrogenpolysiloxanes can be illustrated by the following:

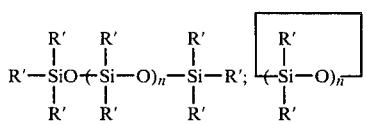

wherein R' is selected from a hydrogen atom, methyl or phenyl, at least two R' groups are hydrogen atoms, and n is a positive integer; copolymers of $R''_2HSiO_{0.5}$ units and $R''SiO_{1.5}$ units; copolymers of $R''_2HSiO_{0.5}$ units, $R''_2SiO$ units and $R''SiO_{1.5}$ units; copolymers of $R''HSiO$ units, $R''_2SiO$ units and $R''SiO_{1.5}$ units; and copolymers of $R''_2HSiO_{0.5}$ units, $SiO_2$ units, and $R''_3SiO_{0.5}$ units wherein each $R''$ is selected from methyl or phenyl. The amount of component (B) added must be an amount sufficient to provide at least 1.5 silcon-bonded hydrogen atoms per one vinyl group in component (A).

Silica which has been treated with dimethyldichlorosilane for hydrophobicity, component (C), is an important component which can improve flame retardancy, transparency, and flow characteristics and which can also impart mechanical strength to the film. The methods using a silica, as a filler, for the silicone rubber varnishes and especially the methods using fumed silica are roughly divided as follows: The method in which hydrophobic silica which has been pretreated with an organosilane compound is compounded into the silicone rubber composition, and the method in which hydrophilic untreated silica is compounded into the silicone rubber composition along with an agent for hydrophobic treatment. When the hydrophilic untreated silica is used along with conventional agents for the hydrophobic treatment, e.g. diorganosiloxanes having terminal hydroxyl groups, hexaorganodisilazanes, and diphenylsilanediol, one of the following items, flame retardancy, flow characteristics, transparency, and bath life of the varnish solution, is impaired and the results of this invention are not achieved. When a silica which has been pretreated with trimethylchlorosilane as in Japanese Patent No. Sho 53(1978)-13505, or a silica which has been pretreated with hexamethyldisilazane as in Kokai Japanese Patent No. Sho 52(1977)-63495, is used, flame retardancy is impaired in spite of excellent transparency. In addition, the bath life of the varnish solution is severely reduced as is evident by the appearance of an insoluble gel matter. Thus, it is difficult to use such a silica treated by the above-mentioned methods. Such drawbacks are more remarkable in the case using silica treated with hexamethyldisilazane. When hydrophobic silica which has been pretreated with dimethyldichlorosilane is used, the compatibility with component (A) is very high and the refractive index of the two components is very close. Surprisingly, a varnish solution with significantly improved transparency and flow characteristics can be produced. No structure formation was found in the varnish solution prepared using this hydrophobic silica for several months and no insoluble gel matter was produced. The flame retardancy and electrical characteristics of woven glass fiber fabrics and glass sleeves which were coated with this varnish were found to be superior. Preferably, the hydrophobic silica which has been pretreated with dimethyldichlorosilane is a fumed silica with the relative surface are of 50 $m^2/g$ or higher. The amount of the silica added ranges from 10 to 100 parts by weight per 100 parts by weight of component (A) and preferably from 30 to 80 parts by weight. If the amount is less or more than this range, the mechanical strength of the varnish film is reduced.

The platinum catalyst used in this invention, component (D), is an indispensable component for accelerating the cross-linking reaction between components (A) and (B) (addition reaction) and for imparting flame retardancy. As platinum, a fine platinum powder, or a platinum powder which is carried on a support such as alumina, silica gel, or asbestos can generally be used. Platinum compounds, for example, chloroplatinic acid or complexes of chloroplatinic acid with alcohols, ethers, aldehydes, and vinylsiloxanes are known. The platinum or platinum compounds must be homogeneously dispersed in the varnish solution. For this reason, platinum or platinum compounds can be dissolved or dispersed in an organic solvent such as isopropyl alcohol, ethanol, benzene, toluene, and xylene, or in an organopolysiloxane oil before use. The amount of this component added appropriately ranges from 1 to 100 ppm relative to component (A) as a platinum equivalence.

Diphenylsilanediol, component (E), acts to permit the use of a larger quantity of component (C) by providing multiple hydrophobic treatments, which results in an increase in viscosity of the varnish solution, and also acts to improve flame retardancy of the varnish film. When this component is used along with the silica filler which has been pretreated with dimethyldichlorosilane for hydrophobicity and the amount of this component is 0.5 to 7 wt % relative to the silica filler, the above-mentioned effects can be obtained satisfactorily. It is characteristic that the addition of this component does not interfere with the transparency of the varnish film.

In addition to the above-mentioned components, other additives can be used, if desirable. For example, compounds such as iron oxide, iron hydroxide, cerium oxide, cerium hydroxide, iron octoate and cerium octoate can be added to the above-mentioned compositions in order to improve heat stability. In order to extend the bath life of the treatment solution, nitrile compounds, azole compounds, and acetylenic alcohols can be added as reaction inhibitors. The compositions of this invention can be easily prepared simply by mixing the above-mentioned components (A) through (D) or components (A) through (E). The order of mixing these components is not particularly critical.

The compositions prepared above can be widely used in a variety of fields. However, the compositions are preferably dissolved or dispersed in an appropriate organic solvent when woven glass fiber fabrics and glass sleeves are to be coated with these compositions. For purposes of this invention, the term "coated" includes "impregnated." A prepared treatment solution is coated using a brush or a spray, and the coated woven glass fiber fabrics and glass sleeves can be cured by heating under the following heating conditions: 100°-200° C. for 5 to 60 minutes. The materials obtained demonstrate excellent transparency, pliability, and flame retardancy.

Examples of this invention will be explained below. "Parts" indicated in these examples implies "parts by weight." In the respective examples, the self-extinguishing property, insulation break strength and flow characteristics of the varnish solution were measured by the following methods.

Self-extinguishing property: A composition was coated on a glass sleeve with an inner diameter of 3 mm and cured by heating. The treated glass sleeve (amount of the composition coated: 35wt. %) was clamped in an almost vertical orientation and ignited by applying a propane burner flame to the lower section of the sleeve for 5 seconds. Then the flame was taken away from the sleeve and the time required for the flame to cease completely (seconds) was determined as a measure of the self-extinguishing character.

Insulation breakdown strength: The data were measured according to JIS C 2122.

Flow characteristics: A varnish solution was tested at speeds of 12 rpm and 30 rpm using a No. 4 rotor and a Model B rotary viscometer (Model Type BM). The viscosities at the respective speeds were measured. The viscosity ratio (viscosity at 12 rpm divided by viscosity at 30 rpm) called the thixo index is used as a measure of the flow characteristics.

EXAMPLE 1

Dimethylvinylsiloxy endblocked polydiorganosiloxane gum (100 parts) having a degree of polymerization of 5000, consisting of 99.84 mol % of dimethylsiloxane units and 0.16 mol % of methylvinylsiloxane units, hydrophobic fumed silica (45 parts) which had been pretreated with dimethyldichlorosilane and which had a relative surface area of 130 m$^2$/g, and methylhydrogenpolysiloxane (3 parts) with an average molecular formula of:

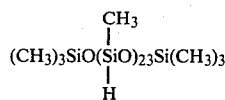

were homogeneously mixed. Chloroplatinic acid hexahydrate was added in an amount such that the proportion of platinum was 30 ppm relative to the mixture. A treatment solution was prepared by dispersing the mixture in xylene to obtain a nonvolatile content of 30 wt. %. Subsequently, a glass sleeve with an inner diameter of 3 mm was coated with this treatment solution using a brush and the coat was cured by drying in a dryer at 150° C. for 15 minutes. This sample was examined with respect to the self-extinguishing property, insulation breakdown strength, and transparency. The results obtained are presented in Table I.

EXAMPLE 2

Dimethylvinylsiloxy endblocked polydiorganosiloxane (100 parts) having a degree of polymerization 5000, consisting of 99.84 mol % of dimethylsiloxane units and 0.16 mol % of methylvinylsiloxane units, hydrophobic fumed silica (60 parts) which had been pretreated with dimethyldichlorosilane and which had a relative surface area of 130 m$^2$/g, methylhydrogenpolysiloxane (5 parts) with an average molecular formula of:
$(CH_3)_3$ SiO $[Si(CH_3)(H)-O]_8$ $[Si(CH_3)_2-O]_{17}$ $Si(CH_3)_3$ and diphenylsilanediol (2 parts) were homogeneously mixed. Chloroplatinic acid hexahydrate added in an amount such that the proportion of platinum was 30 ppm relative to the mixture. A treatment solution was prepared by dispersing the mixture in xylene to obtain a nonvolatile content of 30 wt. %. Subsequently, a treated glass sleeve was prepared by the method described in Example 1. The characteristics as described in Example 1 were examined. The results obtained are presented in Table I.

EXAMPLE 3

Dimethylvinylsiloxy endblocked polydiorganosiloxane (100 parts) having a degree of polymerization 5000, consisting of 89.84 mol % of dimethylsiloxane units, 10.00 mol % of methylphenylsiloxane units and 0.16 mol % of methylvinylsiloxane units, hydrophobic fumed silica (60 parts) which had been pretreated with dimethyldichlorosilane and which had a relative surface area of 130 m$^2$/g, methylhydrogenpolysiloxane (5 parts) with the same average molecular formula as described in Example 2, and diphenylsilanediol (2 parts) were homogeneously mixed. Chloroplatinic acid hexahydrate was added in an amount such that the proportion of platinum was 30 ppm relative to the mixture. A treatment solution was prepared by dispersing the mixture in xylene to obtain a nonvolatile content of 30 wt. %. Subsequently, a treated glass sleeve was prepared by the method described in Example 1. The characteristics as described in Example 1 were examined. The results obtained are presented in Table I.

COMPARATIVE EXAMPLES 1-5

In Comparative Examples 1-5, untreated fumed silica (relative surface area 130 m$^2$/g) that had not been treated with any of the agents commonly used for hydrophobic treatment and hydrophobic fumed silica, (relative surface area 130 m$^2$/g) which had been pretreated with hexamethyldisilazane or trimethylchlorosilane were used instead of hydrophobic silica which had been pretreated with dimethyldichlorosilane used in Examples 1, 2 and 3. The amounts added are shown in Table I. The proportions of other additives mixed were the same as those shown in Table I. Specimens were prepared as described in Example 1. The characteristics as described in Example 1 were examined. The results of the evaluation are presented in Table I.

TABLE 1

|  | Example No. | | | Comparative Example No. | | | | |
|---|---|---|---|---|---|---|---|---|
|  | 1 | 2 | 3 | 1 | 2 | 3 | 4 | 5 |
| Components (parts) | | | | | | | | |
| Vinyl containing polydiorganosiloxane gum | 100 | 100 | — | 100 | 100 | 100 | 100 | 100 |
| Vinyl containing polydiorganosiloxane gum (phenyl) | — | — | 100 | — | — | — | — | — |
| Methylhydrogenpolysiloxane (defined in Example 1) | 3 | — | — | — | — | — | 3 | 3 |
| Methylhydrogenpolysiloxane (defined in Example 2) | — | 5 | 5 | 5 | 5 | 5 | — | — |
| Dimethyldichlorosilane-treated fumed silica | 45 | 60 | 60 | — | — | — | — | — |
| Untreated fumed silica | — | — | — | 60 | 60 | 60 | — | — |

TABLE 1-continued

| | Example No. | | | Comparative Example No. | | | | |
|---|---|---|---|---|---|---|---|---|
| | 1 | 2 | 3 | 1 | 2 | 3 | 4 | 5 |
| Hexamethyldisilazane-treated fumed silica | — | — | — | — | — | — | 45 | — |
| Trimethylchlorosilane-treated fumed silica | — | — | — | — | — | — | — | 45 |
| Dimethylpolysiloxane with terminal hydroxyl groups (0.04 Pa · s) | — | — | — | 15 | — | — | — | — |
| Hexamethyldisilazane | — | — | — | — | 12 | — | — | — |
| Chloroplatinic acid hexahydrate (Pt equivalence) ppm | 30 | 30 | 30 | 30 | 30 | 30 | 30 | 30 |
| Diphenylsilanediol | — | 2 | 2 | — | — | 10 | — | — |
| Characteristics of Varnish Solution | | | | | | | | |
| Solids content (Weight %) | 30 | 30 | 30 | 30 | 30 | 30 | (1) | 30 |
| Viscosity: 12 rpm (Pa · s) | 5.20 | 2.00 | 1.80 | 12.50 | 15.80 | 16.15 | | 9.00 |
| Viscosity: 30 rpm (Pa · s) | 4.68 | 1.78 | 1.63 | 9.61 | 13.16 | 11.06 | | 7.20 |
| Thixo Index | 1.11 | 1.12 | 1.10 | 1.30 | 1.20 | 1.46 | | 1.25 |
| Presence/absence of structure formation | None | None | None | Yes | Yes | None | | None |
| Characteristics of Glass Sleeve Coated with Varnish | | | | | | | | |
| Transparency | Exc. | Exc. | Exc. | Exc. | Exc. | Poor | | Exc. |
| Pliability | " | " | " | " | " | | | Good |
| Insulation breakdown value (KV/0.1 mm) | 5.5 | 6.0 | 5.5 | 4.0 | 4.8 | 5.0 | | 4.6 |
| Flame retardancy (sec.) | 10 | 5 | 7 | (2) | 29 | 41 | | (2) |

(1) Not determined because a homogeneous varnish solution was impossible to obtain due to gel formation
(2) Complete combustion That which is claimed is:

1. A silicone composition consisting essentially of a product obtained by mixing
    (A) 100 parts by weight of a triorganosiloxy endblocked polydiorganosiloxane in which each organic group is selected from methyl, vinyl, and phenyl, there being at least two vinyl groups per molecule, there being no more than 20 mol percent phenyl groups based on the total number of moles of organic groups in the polydiorganosiloxane and said polydiorganosiloxane having a viscosity of at least 0.1 m²/s measured at 25° C.
    (B) an amount of organohydrogenpolysiloxane sufficient to provide at least 1.5 silicon-bonded hydrogen atoms per vinyl group in (A), said organohydrogenpolysiloxane having at least two silicon-bonded hydrogen atoms per molecule, and the organohydrogensiloxane having organic groups selected from methyl and phenyl,
    (C) from 10 to 100 parts by weight of a silica filler having a relative surface area of at least 50 m²/g and having been treated with dimethyldichlorosilane for hydrophobicity, and
    (D) a catalytic amount of a platinum catalyst.

2. The silicone composition in accordance with claim 1 in which the silica filler (C) is present in an amount of from 30 to 80 parts by weight inclusive.

3. The silicone composition in accordance with claim 1 also containing 0.5 to 7 weight percent of diphenylsilanediol based on the weight of (C).

4. The silicone composition in accordance with claim 1 in which the product obtained is dispersed in an organic solvent.

5. The silicone composition in accordance with claim 3 in which the product obtained is dispersed in an organic solvent.

6. The silicone composition in accordance with claim 1 also containing a reaction inhibitor.

7. The silicone composition in accordance with claim 3 also containing a reaction inhibitor.

8. The silicone composition in accordance with claim 4 also containing a reaction inhibitor.

9. The silicone composition in accordance with claim 5 also containing a reaction inhibitor.

10. A method of treating glass fibers comprising
    (I) mixing the following ingredients to make a silicone composition
        (A) 100 parts by weight of a triorganosiloxy endblocked polydiorganosiloxane in which each organic group is selected from methyl, vinyl, and phenyl, there being at least two vinyl groups per molecule, there being no more than 20 mol percent phenyl groups based on the total number of moles or organic groups in the polydiorganosiloxane and said polyorganosiloxane having a viscosity of at least 0.1 m²/s measured at 25° C.
        (B) an amount of organohydrogenpolysiloxane sufficient to provide at least 1.5 silicon-bonded hydrogen atoms per vinyl group in (A), said organohydrogenpolysiloxane having at least two silicon-bonded hydrogen atoms per molecule, and the organohydrogensiloxane having organic groups selected from methyl and phenyl,
        (C) from 10 to 100 parts by weight of a silica filler having a relative surface area of at least 50 m²/g and having been treated with dimethyldichlorosilane for hydrophobicity, and
        (D) a catalytic amount of a platinum catalyst,
    (II) dispersing the silicone composition obtained in step (I) in an organic solvent to make a treatment solution,
    (III) coating glass fibers with the treatment solution obtained in step (II) to make treated glass fibers, and
    (IV) heating the treated glass fibers to cure the silicone composition 11. The method in accordance with claim 10 in which 0.5 to 7 weight percent of diphenylsilanediol based on the weight of (C) is present as an ingredient in step (I).

12. The method in accordance with claim 10 in which the glass fiber is in the form of woven glass fiber fabric.

13. The method in accordance with claim 11 in which the glass fiber is in the form of woven glass fiber fabric.

14. The method in accordance with claim 10 in which the glass fiber is in the form of glass sleeving.

15. The method in accordance with claim 11 in which the glass fiber is in the form of glass sleeving.

16. A treated glass fiber prepared by the method of claim 10.

17. A treated glass fiber prepared by the method of claim 11.

18. A treated woven glass fiber fabric prepared by the method of claim 12.

19. A treated woven glass fiber fabric prepared by the method of claim 13.

20. A treated glass sleeving prepared by the method of claim 14.

21. A treated glass sleeving prepared by the method of claim 15.

* * * * *

UNITED STATES PATENT AND TRADEMARK OFFICE
CERTIFICATE OF CORRECTION

PATENT NO. : 4,340,090

DATED : July 20, 1982

INVENTOR(S) : Takao Matsushita, Kazuo Hirai

It is certified that error appears in the above—identified patent and that said Letters Patent is hereby corrected as shown below:

Column 3, line 11 - the phrase "wherein R'" should read "wherein each R'"

Column 3, line 20 - the phrase "1.5 silcon-" should read "1.5 silicon-"

Column 3, line 65 - phrase "surface are of" should read "surface area of"

Column 8, line 42 - the phrase "moles or organic groups" should read "moles of organic groups"

Signed and Sealed this

Sixteenth Day of November 1982

[SEAL]

Attest:

GERALD J MOSSINGHOFF

Attesting Officer     Commissioner of Patents and Trademarks